United States Patent [19]
Hess et al.

[11] Patent Number: 6,150,085
[45] Date of Patent: Nov. 21, 2000

[54] PROLONGED STORAGE OF RED BLOOD CELLS AND COMPOSITION

[75] Inventors: John R. Hess, Bethesda, Md.; Tibor J. Greenwalt, Cincinatti, Ohio

[73] Assignee: The United States of America as represented by the Secretary of the Army, Washington, D.C.

[21] Appl. No.: 09/154,102

[22] Filed: Sep. 16, 1998

[51] Int. Cl.$^7$ .................................................... A01N 1/02
[52] U.S. Cl. .................................................... 435/2; 604/4
[58] Field of Search .................. 435/2; 604/4; 424/93.73

[56] References Cited

U.S. PATENT DOCUMENTS

| | | | |
|---|---|---|---|
| 4,267,269 | 5/1981 | Grode et al. | 435/2 |
| 5,250,303 | 10/1993 | Meryman et al. | 424/533 |
| 5,906,915 | 5/1999 | Payrat et al. | 435/2 |

FOREIGN PATENT DOCUMENTS

92/08348  5/1992  WIPO .

OTHER PUBLICATIONS

Mazor et al., "Prolonged Storage of Red Cells: The Effect of pH, Adenine and Phosphate", Vox Sang 66: 264–269 (1994).

Hess, John (1996) Extended Liquid Storage of Red Blood Cells. Forum on Blood Safety and Blood Availability, Division of Health Sciences Policy, Institute of Medicine, Manning F. J. and Sparacino, L. (eds), National Academy Press, Washington, D.C. p. 99–102.

Hogman, C. F. et al. (1995) Shall red cell units stand upright, lie flat or be mixed during storage? In vitro studies of red cells collected in 0.5 CPD and stored in RAS2 (Erythrosol®). *Transfus. Sci.* 16:193–199.

Ohkuma, S. et al. (1991) The preservative–exchange method using a sextuple–bag system for a 10–week storage period of red blood cells. *Transfus. Med.* 1:257–262.

Meryman, H. T. et al. (1994) Extending the storage of red cells at 4° C. *Transfus. Sci.* 15:105–115.

Greenwalt, T. J. et al. (1996) Studies in red blood cell preservation 10. $^{51}$Cr recovery of red cells after liquid storage in a glycerol–containing additive solution. *Vox Sang.* 70:6–10.

Dumaswala et al. (1994) Studies in red blood cell preservation 9. The role of glutamine in red cell preservation. *Vox Sang.* 67:255–259.

Dumaswala, U. J. et al. (1996) Glutamine– and phosphate–containing hypotonic storage media better maintain erythrocyte membrane physical properties. *Blood* 88:697–704.

Dumaswala, U. J. et al. (1996) Improved red blood cell preservation correlates with decreased loss of bands 3,4.1, acetylcholinestrase, and lipids in microvesicles. *Blood* 87:1612–1616.

Meryman, H. T. et al. (1986) Prolonged storage of red cells at 4° C. *Transfusion* 26:500–505.

Greenwalt, T. J. et al. (1997) The effect of hypotonicity, glutamine, and glycine on red cell preservation. *Transfusion* 37: 269–276.

*American Association of Blood Banks Technical Manual*, Walker, Richard H., editor in Chief, 1993, p. 52.

*Primary Examiner*—Sandra E. Saucier
*Attorney, Agent, or Firm*—Charles H. Harris; Elizabeth Arwine

[57] ABSTRACT

Novel additive solutions useful for the storage of human red blood cells (RBCs) under refrigerated conditions are disclosed. Also disclosed is a method of using the additive solutions in an appropriate volume to preserve RBCs at about 1 to 6° C. for up to 10 weeks. Additive solutions and processes in accordance with the present invention allow the viable storage of human RBCs for an extended period of time in a solution which is directly infusible in humans.

21 Claims, 2 Drawing Sheets

PROLONGED STORAGE OF RED BLOOD CELLS AND COMPOSITION

INTRODUCTION

Whole blood storage was first demonstrated by Robertson in 1917. Acid-citrate-dextrose (ACD) and Citrate-phosphate-dextrose solution (CPD) were subsequently approved for 21-day storage of blood. CPD with adenine (CPDA-1) was later introduced and used for extending the shelf-life of stored blood for up to 5 weeks. Red blood cells (RBCs) stored in these solutions have shown steady deterioration after about 5 to 6 weeks as determined by the inability of such cells to survive in the circulation for 24 hours after reinfusion back into the human donor. It has been observed that during continued refrigerated storage, glucose is consumed at a decreasing rate, as the concentration of metabolic waste, i.e. lactic acid and hydrogen ions, increases. Such a decrease in the rate of glucose metabolism leads to depletion of adenosine triphosphate (ATP) which directly correlates to the recovery of RBCs when the cells are returned to the circulation.

The development of additive solutions for the preservation of red blood cells (RBCs) after their separation from whole blood has allowed the design of formulations which are specifically tailored to the needs of RBCs. Additive solutions such as Adsol® (AS-1), Nutricel® (AS-3), Opti-sol® (AS-5), and Erythro-Sol® were designed to extend the storage of RBCs at 4° C.

Almost all of the whole blood collected now is made into components, and the RBC fraction is stored as packed RBCs. For blood drawn into the additive solution systems, RBCs are packed by centrifugation, plasma is removed so that RBCs make up 80% of the volume, and then 100 ml of additive solution is added sterilely. The resulting suspensions have a RBC volume fraction of approximately 55%. RBCs stored in the conventional FDA-approved additive solutions can be stored for only 6 weeks with an acceptable 24-hour in vivo recovery.

To increase the in vivo recovery characteristic of RBCs in liquid storage, attempts have been made to improve additive solutions and storage processes. In "Studies In Red Blood Cell Preservation-7. In vivo and In vitro Studies With A Modified Phosphate-Ammonium Additive Solution," by Greenwalt et al., *Vox. Sang.*: 65, 87–94 (1993), the authors determined that the experimental additive solution (EAS-2) containing in mM: 20 $NH_4Cl$, 30 $Na_2HPO_4$, 2 adenine, 110 dextrose, 55 mannitol, pH 7.15, is useful in extending the storage shelf-life of human RBCs from the current standard of 5–6 weeks to an improved standard of 8–9 weeks. However, packed RBCs stored in the medium were not directly infusible but required the removal of the supernatant with a washing step prior to transfusion due to the presence of ammonium in the additive solution.

In "Studies in Red Blood Cell Preservation-8. Liquid Storage of Red Cells in Glycerol-Containing Additive Solution," *Vox. Sang.* 67: 139–143 (1994), Greenwalt et al. described an Experimental Additive Solution 25 (EAS-25) that allowed 73 percent recovery of packed red cells at nine weeks. However, the resulting RBC units contained about 1 percent glycerol and thus, are not safe for transfusion in humans in massive amounts.

In "Extending the Storage of Red Cells at 4° C.," *Transfus. Sci.* 15:105–115 (1994) by Meryman et al., acceptable viability of RBCs stored in very dilute suspensions at low hematocrit for as long as 27 weeks were demonstrated. However, such stored RBC suspensions were not acceptable for direct infusion due to their high content of potassium and ammonia and their low volume fraction of RBCs.

Consequently, there remains a need for improved additive solutions and processes which increase the storage time of human RBCs over that of conventional solutions and processes while allowing the RBC storage suspension to be directly tranfusable into humans and maintaining an acceptable in vivo recovery of RBCs.

SUMMARY OF THE INVENTION

The present invention satisfies the need discussed above. The present invention relates to a novel additive solution useful for the storage of human RBCs under refrigerated conditions. The present invention also relates to a method of using the additive solution to preserve RBCs at about 1 to 6° C. for up to about 10 weeks.

Additive solutions and processes in accordance with the present invention allow the viable storage of human RBCs for an extended period of time in a solution which is directly infusible in humans.

It is, therefore, an object of the present invention to provide an additive solution for storage of human RBCs which solution substantially increases the storage time of the RBCs at about 1 to about 6° C. while maintaining an acceptable recovery of the RBCS.

It is also an object of the present invention to provide an additive solution for storage of human RBCs which is physiologically safe and suitable for direct infusion into humans in massive amounts.

It is yet another object of the present invention to provide a method of storing human RBCs for about 9 to about 10 weeks at about 1 to about 6° C. with an acceptable 24-hour in vivo fractional recovery of the RBCs.

It is also another object of the present invention to provide novel RBC storage suspensions which are directly infusible into humans following about 9 to 10 weeks storage at about 1 to about 6° C.

To achieve the foregoing and other objects in accordance with the purposes of the present invention, we have developed a novel additive solution for preserving RBCs, which solutions comprises an aqueous solution containing adenine, dextrose, $Na_2HPO_4$, mannitol, and at least one physiologically acceptable sodium salt in amounts sufficient to preserve RBCs. The additive solutions are useful in a method for storing RBCs, which method include the steps of:

(a) mixing a sample of whole blood containing the RBCs and plasma with an anticoagulant solution, forming thereby a suspension of whole blood;

(b) treating the whole blood suspension to separate the RBCs from the plasma, forming thereby packed RBCs;

(c) mixing the packed RBCs with an appropriate amount of an additive solution in accordance with the invention thereby forming a suspension of RBCs;

(d) cooling said suspension of RBCs to about 1 to about 6° C.; and (e) storing said cooled suspension of RBCs according to standard blood bank procedures for a period of about 9 to about 10 weeks.

RBC suspensions produced in accordance with the invention after about 9 to about 10 weeks of storage provide a sufficiently therapeutic amount of recoverable RBCs and are directly infusible into humans without further processing in accordance with known standards established for transfusion of RBCs.

DETAILED DESCRIPTION OF THE INVENTION

Figure 1:
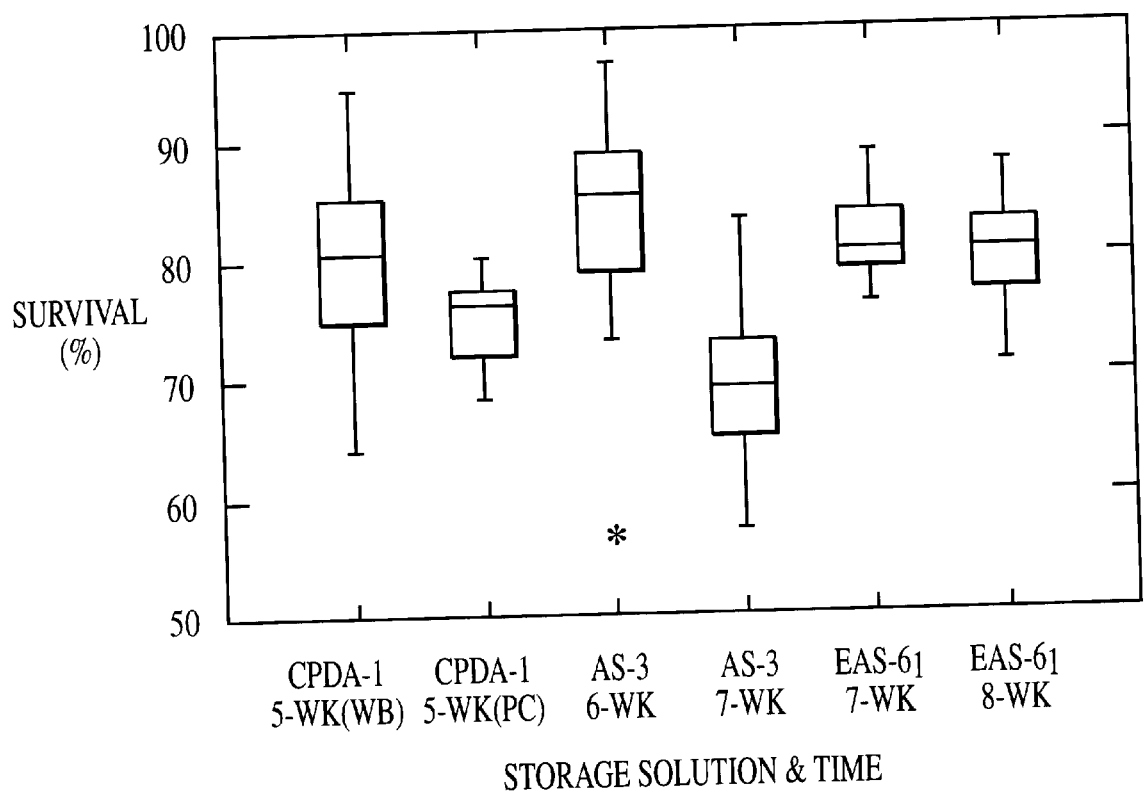
FIG. 1 demonstrates the 24 hour in vivo recovery of RBCs stored in a variety of solutions for periods ranging from 5 to 8 weeks.

For purposes of this invention, the term "recovery" is used herein to indicate the fraction of stored RBCs that remains in circulation for 24 hours after re-infusion into a human donor.

The term "prolonged" or "extended" storage is used herein to indicate the preservation or storage of RBCs for a period of time greater than 6 weeks up to about 10 weeks with an acceptable recovery of RBCs.

An additive solution in accordance with the invention comprises an aqueous solution of adenine, dextrose, $Na_2HPO_4$, mannitol, and at least one physiologically acceptable sodium salt, in concentrations suitable to preserve RBCs. In general, the solution contains adenine from about 1 to 3 mM, dextrose from about 20 to 115 mM, $Na_2HPO_4$ from about 4 to 15 mM, mannitol from about 15 to 60 mM, and at least one physiologically acceptable sodium salt from about 20 to 130 mM. Preferably, adenine is about 2 mM, dextrose is about 50 to 110 mM, $Na_2HPO_4$ is about 9 to 12 mM, mannitol is about 20 to 50 mM, and at least one physiologically acceptable sodium salt is about 25 to 75 mM. A combination of $Na_2HPO_4$ and $NaH_2PO_4$ can also be used.

Suitable sodium salts useful in the medium of the invention include those salt compounds containing a sodium cation which are physiologically acceptable in humans. Preferred sodium salts include sodium chloride, sodium acetate, sodium citrate and the like. Most preferably, the medium contains about 20 to 100 M of sodium chloride and 0 to 53 mM of sodium acetate.

The pH of the additive solution is maintained in a range of about 7 to 9 at room temperature. Preferably, the pH of the additive solution of the invention is in the range of about 8 to 8.8. Most preferably, the pH of the additive solution is about 8.4 to about 8.6.

The osmolarity of the suspension medium of the invention is in the range of about 200 to 310 mOsm. Preferably, the osmolarity is in the range of about 221 to 280 mOsm. Most preferably, the osmolarity of the additive solution is about 240 to 256 mOsm.

RBCs useful in the present invention are those which have been separated from their plasma and resuspended in an anticoagulant solution in the normal course of component manufacture. Briefly stated, a standard whole blood sample (450±50 ml) containing RBCs and plasma is mixed with an anticoagulation solution (about 63 ml) to form a suspension of whole blood. The whole blood suspension is thereafter centrifuged to separate the RBCs from the blood plasma thereby forming a packed RBCs.

Suitable anticoagulants include conventional anticoagulants known for storage of RBCs. Preferably, the anticoagulants include citrate anticoagulants having a pH of 5.5 to 8.0, e.g. CPD, half-strength CPD and the like. The most preferred anticoagulant is CPD.

In accordance with the method of the invention, additive solution is added to the packed RBC suspension in an amount sufficient to provide a therapeutic effective amount of recoverable RBCs in the cell suspension. Preferably, the additive solution is added at a volume ranging from about 140 ml to about 400 ml, preferably about 180 to about 300 ml, most preferably 200 ml.

The RBC volume fraction in the cell suspension, i.e. after addition of additive solution, is about 27 to 50% of the total suspension. More preferably, the RBC volume fraction in the cell suspension is about 35 to about 45%. Most preferably, the RBC volume fraction in the cell suspension is about 43% of the total suspension.

The RBC suspension is then stored in standard polyvinyl chloride (PVC) blood storage bags using either the collection bag or PVC transfer packs of different sizes depending on the volume of the stored aliquot. The RBC suspension is stored at about 1 to 6° C. according to standard blood bank procedure as described in *Clinical Practice of Blood Transfusion* editors: Petz & Swisher, Churchill-Livingston publishers, N.Y., 1981. All documents cited herein infra and supra are hereby incorporated by reference thereto.

Without being bound to any particular theory or explanation, it is believed that when stored in large volumes of additive solution in accordance with the invention, the increased volume of nutrient solution allows an increased mass of substrate to be delivered at acceptable concentrations while providing solute for dilution of metabolic waste products thereby reducing feedback inhibition of glucose metabolism.

It is further postulated that another feature of the additive solutions of the invention is that they produce swelling of the RBCs initially followed by a gradual reduction of red cell volume during storage. Such a process has been called "regulated volume decrease". It is hypothesized that during this process either the tyrosine phosphatase activity present in the RBC is suppressed or the tyrosine kinase is activated. Both of these enzymes have been demonstrated to be abundant in the membranes of these cells [Zipser, Y. and Kosower, N. S. (1996) *Biochem. J.* 314:881; Mallozzi C. et al. (1997) *FASEB J.* 11: 1281]. It is anticipated that the net phosphorylation of the band 3 protein in the RBC membrane would result in the release of phosphofructokinase, aldolase and glyceraldehyde-3-phosphate dehydrogenase in the cytoplasm from their bound state to band 3 [Harrison, M. L. et al. (1991) *J. Biol. Chem.* 266:4106; Cossins, A. R. and Gibson J. S. (1997) *J. Exper. Biol.* 200:343; Low, P. S. et al. (1993) *J. Biol. Chem.* 268: 14627; Low, P. S. et al. (1995) *Protoplasma* 184:196]. The availability of these three enzymes in the glycolytic pathway would be expected to increase the metabolism of glucose by the RBC, thereby promoting acceptable levels of ATP levels in the RBCs.

It is understood that the examples and embodiments described herein are for illustrative purposes only and that various modifications or changes in light thereof are to be included within the spirit and purview of this application and the scope of the appended claims.

The following Materials and Methods were used in the Examples which follow.

Preparation of Additive Solution: Additive solutions in accordance with the present invention were prepared by mixing the components in an aqueous solution. Adenine was obtained from Sigma Chemical (St. Louis, Mo.). The other chemicals used were of ACS grade and were obtained from Fisher Scientific (Cincinnati, Ohio). Sterility of the additive solution was achieved by filtration through a 0.22-um filter with a filling bell (Sterivex-GX, Millipore Corporation, Bedford, Mass.) into a 1-L sterile transfer packs (Baxter Healthcare, Ill.). Sterility was established by culture.

The pH was-measured using an Orion pH meter (Model 900A Analytical Technology, Inc., Orion, Boston, Mass.). The osmolalities were measured by freezing point depression (Osmette TM Precision Systems, Sudbury, Mass.).

Blood Samples: Blood donors acceptable by the American Association of Blood Banks and Food and Drug Administration criteria were used. Standard units of blood (450 ml) were collected with 63 ml CPD polyvinyl-chloride bags. Each unit of whole blood was centrifuged and the platelet-rich plasma expressed into a satellite bag. Additive solutions in the stated volume were added and the unit stored at 1–6° C. for the stated period.

In vivo testing: After storage, in vivo RBC recovery was measured 24 hours after autologous reinfusion using a double radioisotope procedure [Moroff, G. et al. (1984) *Transfusion* 24:109–114; International Committee on Standarization in Hematology. Recommended Method for Radioisotope Red-Cell Survival Studies. *Brit. J. Haematology* (1980) 45:659–666]. In brief, a sample of the stored blood was labeled with $^{51}Cr$. Concurrently, a fresh blood sample was collected from the volunteer and labeled with $^{99m}Tc$ (Ultratag RBC kit for the preparation of Technitium Tc-99m, labeled red blood cells package insert. Mallinckrodt Medical, St. Louis, Mo.). Carefully measured aliquots of the radiolabeled red cells were mixed and rapidly reinfused. Blood samples were collected at timed intervals during the 60 minutes immediately following the reinfusion and again at 24 hours. Radioactivity of the samples was measured in a gamma counter (Wallac CLINGAMMA Twin 2, Model 1272, Turku, Finland). Gamma emissions from $^{99m}Tc$ radio-labeled cells were measured in the samples collected during the 30 minutes following reinfusion and used to determine an independent RBC volume. The activity from $^{51}Cr$ labeled cells was measured in the delayed samples and used to calculate the recovery of the transfused RBCs. The results were expressed as 24-hour in vivo recovery percentage of RBC.

EXAMPLE I

RBC recovery after storage was measured as the autologous 24-hour recovery fraction. Whole blood stored in CPDA-1 for 5 weeks, packed red blood cells stored in CPDA-1 for 5 weeks, packed red blood cells stored in AS-3 solution for 6 and 7 weeks, were compared to 7 to 8-week storage of packed red blood cells in EAS-61, an additive solution according to the present invention.

The components of EAS-61 are described in Table 1 below. The pH of the solution at room temperature was 8.58 and the measured total osmolarity was 256 mOsm/Kg $H_2O$.

TABLE 1

| Composition of EAS-61 additive solution | |
|---|---|
| Adenine | 2 mM |
| Dextrose | 110 mM |
| $Na_2HPO_4$ | 12 mM |
| Mannitol | 55 mM |
| NaCl | 26 mM |

Ten volunteers had their blood stored in additive solution EAS-61 for seven weeks and ten for eight weeks.

Results (shown in FIG. 1) indicate that 24-hour in vivo recovery percentage of RBC stored in 200 ml of the additive solution of the invention was over 80% after 7 and 8 weeks of storage. By comparison, percentage RBC recovery in 100 ml of AS-3 after 7 weeks of storage was less than about 70%, and in CPDA-1 with no additive solution, less than 80% after only 5 weeks of storage of packed RBCs. Values for the licensed solutions are from the referenced literature found in the legend to FIG. 1.

EXAMPLE 2

The RBC recovery after storage for 8 and 9 weeks in EAS-61 was also determined. Two hundred mls of the additive solution was added to packed cells from one unit of blood and stored at 1 to 6° C. The results of in vivo testing of ten units at eight weeks and ten units at nine weeks were expressed as 24-hour in vivo recovery percentage of RBC and are recorded in FIG. 2.

Figure 2:
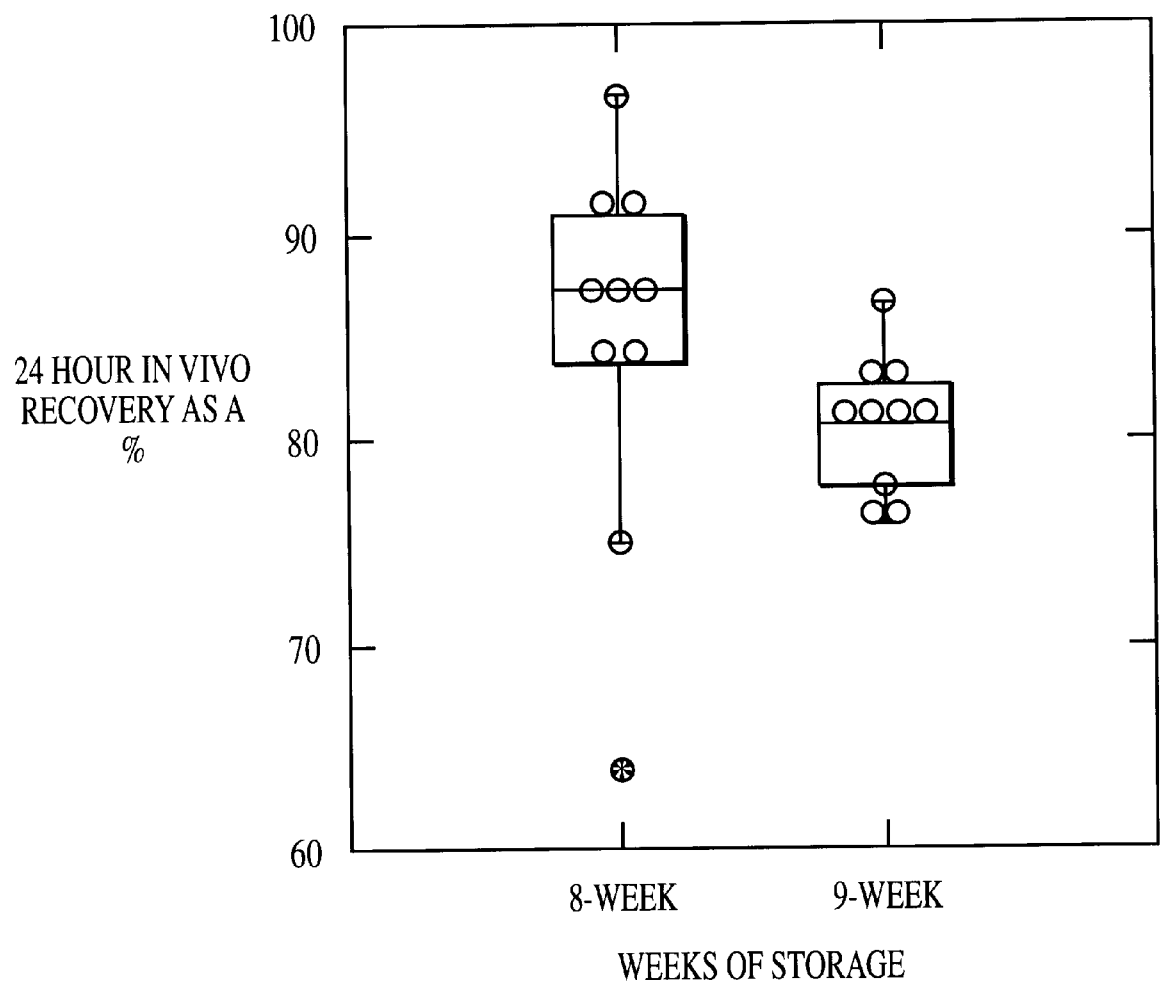
FIG. 2 demonstrates the 24 hour in vivo recovery of RBCs stored in EAS-61, an additive solution according to the present invention, for periods ranging from 8 to 9 weeks.

As shown in FIG. 2, the percentage recovery of RBCs stored in 200 ml of the additive solution of the invention was 81% after 9 weeks of storage.

Results indicate that RBCs can be stored for at least nine weeks in 200 ml of additive solution according to the present invention with satisfactory in vivo recovery.

EXAMPLE 3

Attempts to increase the useful shelf-life of strored RBCs are in progess both by increasing the volume of the additive solution and by altering the concentrations of different salts in the solution, namely NaCl and NaAcetate.

In vitro tests will be performed on additive solutions in accordance with the invention at various volume levels. In vitro measurements will include spun hematocrit, supernatant hemoglobin, percent hemolysis, milliosmolality of the additive solutions and the supernatant after the additive solution is mixed with the blood, complete blood counts (CBCs), mean corpuscular volume (MCV), mean corpuscular hemoglobin concentration (MCHC), extra- and intracorpuscular pH, quantitation of adenosine-5-triphosphate (ATP), DPG (2,3-diphosphoglycerate), glucose, potassium, inorganic phosphate (Pi) and lactic acid and RBC morphology.

In vitro studies using increasing volumes of the additive solution as described in Table 2 below are now in progress.

Data (summarized in Tables 3–6) for up to 3 weeks of storage of RBCs in increased volumes of up to 400 mls of EAS-64, an additive solution according to the present invention described in Table 2 suggest improved storage as indicated by the increased ATP values and the low hemolysis and potassium leakage.

TABLE 2

| Composition of additive solution EAS-64 | |
|---|---|
| Adenine | 2 mM |
| Dextrose | 50 mM |
| $Na_2HPO_4$ | 9 mM |
| Mannitol | 20 mM |
| NaCl | 75 mM |

TABLE 3

In vitro Data: RBC Stored in 100 ml of EAS-64

| | 1 HR | 1WK | 2WK | 3WK |
|---|---|---|---|---|
| ATP(umoles/g Hgb) | 4.10 ± 0.25 | 4.26 ± 0.11 | 4.30 ± 0.11 | 4.07 ± 0.15 |
| % ATP | — | 104 ± 5 | 105 ± 5 | 100 ± 5 |
| % Hemolysis | 0.04 ± 0.02 | 0.08 ± 0.03 | 0.11 ± 0.03 | 0.15 ± 0.07 |
| Extracellular pH | 7.29 ± 0.01 | 7.21 ± 0.09 | 7.08 ± 0.02 | 6.95 ± 0.03 |
| Potassium (mEq/L) | 2.1 ± 0.3 | 17.0 ± 3.9 | 24.3 ± 3.9 | 33.1 ± 1.3 |

TABLE 3-continued

In vitro Data: RBC Stored in 100 ml of EAS-64

|  | 1 HR | 1WK | 2WK | 3WK |
|---|---|---|---|---|
| Glucose (mg/dL) | 556 ± 14 | 484 ± 15 | 427 ± 15 | 384 ± 20 |
| Lactic Acid(mmol/L) | 4.2 ± 0.5 | 12.8 ± 0.7 | 18.4 ± 1.9** | 20.4 ± 1.5 |
| Phosphate (mg/dL) | 20.8 ± 2.0 | — | — | — |
| Spun Hct (%) | 64 ± 1 | 64 ± 1 | 64 ± 1 | 64 ± 1 |
| MCV (fL) | 107.6 ± 4.5 | 105.2 ± 4.0 | 105.0 ± 4.4 | 104.8 ± 5.1 |
| MCHC (g/dL) | 28.2 ± 0.7 | 28.2 ± 0.6 | 28.4 ± 0.6 | 28.4 ± 0.6 |

Values are Mean ± SD; n = 6
*n = 5

TABLE 4

In vitro Data: RBC Stored in 200 ml of EAS-64

|  | 1 HR | 1WK | 2WK | 3WK |
|---|---|---|---|---|
| ATP(umoles/g Hgb) | 4.52 ± 0.22 | 4.74 ± 0.15 | 4.88 ± 0.17 | 4.67 ± 0.26 |
| % ATP | — | 105 ± 3 | 108 ± 4 | 104 ± 5 |
| % Hemolysis | 0.04 ± 0.01 | 0.06 ± 0.02 | 0.09 ± 0.02 | 0.13 ± 0.05 |
| Extracellular pH | 7.24 ± 0.02 | 7.14 ± 0.02 | 7.03 ± 0.04 | 6.95 ± 0.04 |
| Potassium* (mEq/L) | below detection | 11.6 ± 2.6 | 15.8 ± 2.5 | 21.8 ± 0.8 |
| Glucose (mg/dL) | 659 ± 18 | 598 ± 15 | 559 ± 15 | 527 ± 14 |
| Lactic Acid(mmol/L) | 3.2 ± 0.4 | 10.1 ± 0.5 | 14.5 ± 1.2** | 16.9 ± 1.5 |
| Phosphate (mg/dL) | 25.8 ± 1.7 | — | — | — |
| Spun Hct (%) | 51 ± 1 | 51 ± 1 | 51 ± 1 | 51 ± 1 |
| MCV (fL) | 112.8 ± 5.3 | 109.7 ± 3.5 | 110.5 ± 4.0 | 110.2 ± 3.9 |
| MCHC (g/dL) | 26.8 ± 0.8 | 27.2 ± 0.5 | 27.1 ± 0.7 | 27.1 ± 0.6 |

*Corrected for dilution. Values are Mean ± SD; n = 6
**n = 5

TABLE 5

In vitro Data: RBC Stored in 300 ml of EAS-64

|  | 1 HR | 1WK | 2WK | 3WK |
|---|---|---|---|---|
| ATP(umoles/g Hgb) | 4.82 ± 0.33 | 5.08 ± 0.21 | 5.20 ± 0.18 | 5.06 ± 0.27 |
| % ATP | — | 106 ± 3 | 108 ± 5 | 105 ± 7 |
| % Hemolysis | 0.04 ± 0.01 | 0.07 ± 0.03 | 0.10 ± 0.02 | 0.15 ± 0.05 |
| Extracellular pH | 7.28 ± 0.04 | 7.15 ± 0.02 | 7.04 ± 0.03 | 6.96 ± 0.03 |
| Potassium* (mEq/L) | below detection | 9.6 ± 2.2 | 13.2 ± 2.0 | 18.3 ± 0.6 |
| Glucose (mg/dL) | 702 ± 12 | 660 ± 13 | 632 ± 16 | 606 ± 14 |
| Lactic Acid(mmol/L) | 2.9 ± 0.4 | 9.2 ± 0.5 | 13.1 ± 0.9** | 16.1 ± 1.3 |
| Phosphate (mg/dL) | 31.5 ± 1.8 | — | — | — |
| Spun Hct (%) | 43 ± 1 | 43 ± 1 | 43 ± 1 | 42 ± 1 |
| MCV (fL) | 116.4 ± 5.8 | 115 ± 4.7 | 114.7 ± 5.0 | 113.6 ± 4.3 |
| MCHC (g/dL) | 26.1 ± 0.7 | 26.3 ± 0.8 | 26.3 ± 0.8 | 26.4 ± 0.5 |

*Corrected for dilution. Values are Mean ± SD; n = 6
**n = 5

TABLE 6

In vitro Data: RBC Stored in 400 ml of EAS-64

|  | 1HR | 1WK | 2WK | 3WK |
|---|---|---|---|---|
| ATP(umoles/g Hgb) | 4.96 ± 0.21 | 5.27 ± 0.29 | 5.47 ± 0.16 | 5.22 ± 0.32 |
| % ATP | — | 107 ± 4 | 110 ± 3 | 105 ± 7 |
| % Hemolysis | 0.05 ± 0.02 | 0.08 ± 0.02 | 0.11 ± 0.03 | 0.16 ± 0.06 |
| Extracellular pH | 7.26 ± 0.03 | 7.18 ± 0.02 | 7.08 ± 0.05 | 6.98 ± 0.05 |
| Potassium* (mEq/L) | below detection | 8.4 ± 1.8 | 11.7 ± 1.7 | 15.9 ± 0.7 |
| Glucose (mg/dL) | 733 ± 16 | 699 ± 22 | 684 ± 16 | 659 ± 12 |
| Lactic Acid*(mmol/L) | 2.7 ± 0.3 | 8.3 ± 0.4 | 12.1 ± 0.6** | 14.5 ± 0.9 |
| Phosphate (mg/dL) | 36.4 ± 1.8 | — | — | — |
| Spun Hct (%) | 36 ± 1 | 36 ± 1 | 36 ± 1 | 36 ± 1 |
| MCV (fL) | 118.2 ± 7.3 | 116.7 ± 4.9 | 116.0 ± 4.3 | 115.7 ± 4.6 |
| MCHC (g/dL) | 25.8 ± 0.9 | 25.9 ± 0.8 | 26.0 ± 0.5 | 26.0 ± 0.6 |

*Corrected for dilution. Values are Mean ± SD; n = 6
**n = 5

These results indicate that dilution is at least partly responsible for the excellent recoveries achieved with the additive solutions of the invention. Further in vitro and in vivo studies are in progress to determine the best volume and composition for storage of RBCs for up to about 11 weeks.

What is claimed is:

1. An additive solution for prolonged storage of red blood cells at 1 to 6° C., said solution consisting essentially of adenine at 1 to 3 mM, dextrose at 20 to 115 mM, $Na_2HPO_4$ at 4 to 15 mM, mannitol at 15 to 60 mM, and 20–130 mM of a physiologically acceptable sodium salt wherein the pH is 8.0 to 8.8 measured at room temperature.

2. The suspension medium according to claim 1 wherein, said solution has an osmolarity of about 200 to about 310.

3. The suspension medium of claim 2 wherein the osmolarity is about 221 to about 280 mOsm.

4. The suspension medium of claim 3 wherein the osmolarity is about 240 to 256 mOsm.

5. The suspension medium of claim 1 wherein the pH is 8.4 to 8.6.

6. A method of preserving red blood cells (RBCs) for an extended period of time comprising:
   (a) mixing a sample of whole blood containing the RBCs to be stored and plasma with an anticoagulant solution, forming thereby a suspension of whole blood;
   (b) treating the whole blood suspension to concentrate the RBCs from the plasma, forming thereby packed RBCs;
   (c) mixing the packed RBCs with an appropriate amount of an additive solution consisting essentially of adenine at 1 to 3 mM, dextrose at 20 to 115 mM, $Na_2HPO_4$ at 4 to 15 mM, mannitol at 15 to 60 mM, and 20–130 mM of a physiologically acceptable sodium salt, said solution having an osmolarity of 200 to about 310 mOsm and a pH of 8 to about 8.8 measured at room temperature, thereby forming a suspension of RBCs;

(d) cooling said suspension of RBCs to 1 to about 6° C.; and (e) storing said cooled suspension of RBCs according to standard blood bank procedures for a period of 8 to about 10 weeks.

7. The method of claim 6 wherein the osmolarity is about 221 to 280 mOsm.

8. The method of claim 7 wherein the osmolarity is about 240 to 256 mOsm.

9. The method of claim 6 wherein the pH is 8.4 to 8.6 measured at room temperature.

10. The method of claim 6 wherein the concentration of RBCs in the RBC suspension is about 25 to about 50% of the total suspension.

11. The method of claim 10 wherein the concentration of RBCs in the RBC suspension is 35 to about 45 of the total suspension.

12. The method of claim 10 wherein the concentration of RBCs in the RBC suspension is about 43% of the total suspension.

13. A directly infusible red blood cell storage suspension comprising red blood cells (RBCs) suspended in a solution comprising adenine at 1 to 3 mM, dextrose at 20 to 115 mM, $Na_2HPO_4$ at 4 to 15 mM, mannitol at 15 to 60 mM, and 20–130 mM of a physiologically acceptable sodium salt chosen from the group consisting of: sodium chloride and sodium acetate.

14. The infusible suspension of red blood cells (RBCs) according to claim 13 wherein said solution has an osmolarity of about 200 to about 310 mOsm and a pH of 8 to 9, and wherein the volume fraction of RBCs suspended in the solution is 25 to 50% of the total solution.

15. The infusible suspension of claim 14 wherein the suspension has been stored for 8 to 9 weeks at a temperature of 1 to 6° C.

16. An additive solution for prolonged storage of red blood cells at 1 to 6° C., said solution consisting essentially of adenine at 2 mM, dextrose at 110 mM, $Na_2HPO_4$ at 12 mM, mannitol at 55 mM, and 26 mM of a physiologically acceptable sodium salt wherein the pH is 8.0 to 8.8 measured at room temperature.

17. A directly infusible red blood cell suspension comprising red blood blood cells suspended in the solution of claim 16.

18. The additive solution according to claim 16, wherein said sodium salt is sodium chloride.

19. An additive solution for prolonged storage of red blood cells at 1 to 6° C., said solution consisting essentially of adenine at 2 mM, dextrose at 50 mM, $Na_2HPO_4$ at 9 mM, mannitol at 20 mM, and 75 mM of a physiologically acceptable sodium salt wherein the pH is 8.0 to 8.8 measured at room temperature.

20. A directly infusible red blood cell suspension comprising red blood blood cells suspended in the solution of claim 19.

21. The additive solution according to claim 19 wherein said sodium salt is sodium chloride.

* * * * *